United States Patent
Pinsky et al.

(10) Patent No.: US 9,659,186 B2
(45) Date of Patent: *May 23, 2017

(54) CONTROLLED USE MEDICAL APPLICATION

(71) Applicant: Schwegman Lundberg & Woessner, P.A., Minneapolis, MN (US)

(72) Inventors: Howard Pinsky, Mansfield, MA (US); Gen-nan Chen, Foster City, CA (US); Daniel A. Halpern, Saint Louis Park, MN (US); Stephen J. Swartz, Maple Grove, MN (US); Trent W. Henson, Cypress, TX (US)

(73) Assignee: Schwegman, Lundberg & Woessner, P.A, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/513,252

(22) Filed: Oct. 14, 2014

(65) Prior Publication Data

US 2015/0033363 A1 Jan. 29, 2015

Related U.S. Application Data

(63) Continuation of application No. 12/697,152, filed on Jan. 29, 2010, now Pat. No. 8,893,120.

(51) Int. Cl.
G06F 9/445 (2006.01)
G06F 21/62 (2013.01)
G06F 19/00 (2011.01)

(52) U.S. Cl.
CPC ............ *G06F 21/6245* (2013.01); *G06F 8/61* (2013.01); *G06F 9/445* (2013.01); *G06F 19/3406* (2013.01)

(58) Field of Classification Search
CPC ........ G06F 9/445; G06F 21/6245; G06F 8/61; G06F 19/3406
See application file for complete search history.

(56) References Cited

U.S. PATENT DOCUMENTS 5,258,906 A 11/1993 Kroll et al.
5,668,998 A 9/1997 Mason et al.
(Continued)

OTHER PUBLICATIONS

"U.S. Appl. No. 12/697,134, Non Final Office Action mailed Jul. 13, 2012", 21 pgs.
(Continued)

*Primary Examiner* — Jing-Yih Shyu
(74) *Attorney, Agent, or Firm* — Schwegman Lundberg & Woessner, P.A.

(57) ABSTRACT

Various systems, machine-readable media, and methods for controlled use of medical applications using virtualization are described herein. In various embodiments, a virtualized medical application container can be created, including creating an image of a clean version of an operating system, installing a medical application on the image, and initializing the medical application on the image. Various embodiments include receiving an indication of a request for metered use of the medical application; requesting permission for metered use of the medical application, wherein the metered use includes at least one of a single use, a defined number of uses, unlimited use, or timed use; executing at least a portion of the medical application; and controlling usage of the medical application to comply with at least one of medical informatics standards and medical informatics regulations.

22 Claims, 5 Drawing Sheets

(56) References Cited

U.S. PATENT DOCUMENTS

| | | |
|---|---|---|
| 5,949,999 A | 9/1999 | Song et al. |
| 6,253,375 B1 | 6/2001 | Gordon et al. |
| 6,829,378 B2 | 12/2004 | DiFilippo et al. |
| 6,829,704 B2 | 12/2004 | Zhang et al. |
| 6,966,000 B2 | 11/2005 | Zhang et al. |
| 6,983,375 B2 | 1/2006 | Zhang et al. |
| 6,990,434 B2 | 1/2006 | Minogue et al. |
| 7,020,868 B2 | 3/2006 | Debbins et al. |
| 7,095,854 B1 | 8/2006 | Ginter et al. |
| 7,099,801 B1 | 8/2006 | McBride et al. |
| 7,113,894 B2 | 9/2006 | Minogue et al. |
| 7,187,790 B2 | 3/2007 | Sabol et al. |
| 7,194,371 B1 | 3/2007 | McBride et al. |
| 7,349,856 B2 | 3/2008 | Ackermann et al. |
| 7,421,516 B2 | 9/2008 | Minogue et al. |
| 7,634,561 B2* | 12/2009 | Brans .................... G06F 9/4862 705/52 |
| 8,176,482 B1 | 5/2012 | Felix |
| 2002/0010597 A1* | 1/2002 | Mayer ................... G06F 19/322 705/2 |
| 2002/0028007 A1 | 3/2002 | Gendron et al. |
| 2002/0065685 A1* | 5/2002 | Sasaki ................. A61M 15/025 705/3 |
| 2002/0091547 A1 | 7/2002 | Ohe et al. |
| 2004/0139024 A1 | 7/2004 | So |
| 2005/0060722 A1 | 3/2005 | Rochette et al. |
| 2005/0062603 A1* | 3/2005 | Fuerst .............. G06K 19/07758 340/539.12 |
| 2005/0074157 A1* | 4/2005 | Thomas, III ........... A61B 8/461 382/132 |
| 2005/0182660 A1* | 8/2005 | Henley ................. G06F 19/327 705/2 |
| 2006/0004745 A1* | 1/2006 | Kuhn .................... G06Q 10/10 |
| 2006/0161457 A1 | 7/2006 | Rapaport et al. |
| 2007/0230829 A1 | 10/2007 | Sirohey et al. |
| 2007/0234295 A1 | 10/2007 | Dufour et al. |
| 2008/0004992 A1 | 1/2008 | King et al. |
| 2008/0006282 A1 | 1/2008 | Sukovic et al. |
| 2008/0033751 A1* | 2/2008 | Greene ................. G06F 19/328 705/2 |
| 2008/0046378 A1 | 2/2008 | Harrison et al. |
| 2008/0109250 A1* | 5/2008 | Walker ................ G06F 17/2247 705/2 |
| 2008/0183641 A1* | 7/2008 | Tang ................... G06F 9/45537 705/418 |
| 2008/0216175 A1 | 9/2008 | Pike |
| 2008/0301676 A1 | 12/2008 | Alpern et al. |
| 2009/0113413 A1 | 4/2009 | Reinz et al. |
| 2009/0132586 A1* | 5/2009 | Napora ................. G06F 19/322 |
| 2010/0049637 A1* | 2/2010 | Laventman ............ G06Q 10/06 705/30 |
| 2010/0064299 A1 | 3/2010 | Kacin et al. |
| 2010/0125667 A1 | 5/2010 | Govindarajan |
| 2010/0228903 A1 | 9/2010 | Chandrasekaran et al. |
| 2010/0228934 A1 | 9/2010 | Chandrasekaran et al. |
| 2010/0250869 A1 | 9/2010 | Adams et al. |
| 2010/0250895 A1 | 9/2010 | Adams et al. |
| 2010/0306379 A1* | 12/2010 | Ferris ................... G06F 9/5072 709/226 |
| 2011/0055378 A1* | 3/2011 | Ferris ................. G06F 11/3409 709/224 |
| 2011/0106881 A1* | 5/2011 | Douville ................. G06F 8/61 709/203 |
| 2011/0191767 A1 | 8/2011 | Pinsky et al. |
| 2011/0191821 A1 | 8/2011 | Pinsky et al. |
| 2011/0191822 A1 | 8/2011 | Pinsky et al. |

OTHER PUBLICATIONS

"U.S. Appl. No. 12/697,143, Non Final Office Action mailed Jul. 19, 2012", 14 pgs.

"U.S. Appl. No. 12/697,152, Examiner Interview Summary mailed Feb. 26, 2014", 3 pgs.

"U.S. Appl. No. 12/697,152, Final Office Action mailed Dec. 19, 2013", 18 pgs.

"U.S. Appl. No. 12/697,152, Non Final Office Action mailed Mar. 26, 2013", 20 pgs.

"U.S. Appl. No. 12/697,152, Notice of Allowance mailed Jul. 10, 2014", 10 pgs.

"U.S. Appl. No. 12/697,152, Response filed May 19, 2014 to Final Office Action mailed Dec. 19, 2013", 13 pgs.

"U.S. Appl. No. 12/697,152, Response filed Sep. 26, 2013 to Non Final Office Action mailed Mar. 26, 2013", 16 pgs.

"K-PACS", Retrieved from the Internet <URL:http://web.archive.org/web/20090224215914/http://k-pacs.net>, (2009), 1-2.

Duenas, Juan C., et al., "System Virtualization Tools for Software Development", IEEE Internet Computing, (2009).

Galan, Fennfn, et al., "Use of Virtualization Tools in Computer Network laboratories", (2004).

Langer, et al., "DCMTB: A virtual Applicance DICOM Toolbox, Aug. 2009", Retrieved from the Inernet <URL: ncbi.nlm.nih.gov/pmc/articles/PMC3046693/pdf/10278_2009_Article_9230.pdf>, 1-8.

Yu, "OS-level virtualization and Its Applications", Retrieved from the Internet <URL: proquest.umi.com/pqdweb?did=1633767911&sid=1&Fmt=2&clientId=19649&RQT =309&VName=POD,, 1-135.

* cited by examiner

CONTROLLED USE MEDICAL APPLICATION

CLAIM OF PRIORITY

This application claims the benefit of priority to, and is a continuation of, U.S. application Ser. No. 12/697,152, filed Jan. 29, 2010, issued as U.S. Pat. No. 8,893,120 on Nov. 18, 2014, which is hereby incorporated by reference herein in its entirety.

BACKGROUND

A large number and variety of software-based medical applications have been developed by academic and commercial entities for use in a variety of areas in the medical field, including patient diagnostics, results reporting, treatment planning, post-procedure follow-up, and clinical operations. Medical applications can, among other things, provide immediate or convenient access to laboratory or imaging tests, provide evidence-based clinical decision-making tools, or address operational efficiencies in healthcare by reducing paperwork or providing logistical support.

For example, information used by a clinician or a specialist for a patient evaluation or consultation is often based on data from one or more prior consultations, or from one or more previous diagnostic tests. However, in certain examples, data collected from one clinician or medical system can be incompatible or incomplete for use by another clinician or medical system. In these examples, the patient could benefit if additional data could be used across different settings in healthcare organizations. Healthcare informatics attempts to deal with this and other problems by merging information science, computer science, and health care to optimize, among other things, the acquisition, storage, retrieval, display, or use of information in healthcare or biomedicine.

In an example, data from a first medical system can be formatted for use by a second medical system. However, creating specific ad-hoc interfaces for each combination of medical systems is largely impractical and a poor solution. Accordingly, medical standards pertaining to the collection, manipulation, or transmission of healthcare information have been developed to improve interoperability between disparate medical systems.

Medical applications typically provide support for at least one medical standard. In certain examples, the support can include an interface for sending or receiving medical data according to one or more applicable medical standard. Examples of medical standards include Digital Imaging and Communications in Medicine (DICOM) or Health Level Seven (HL7), Integrated Healthcare Enterprise (IHE) among others.

For example, DICOM is a standard for handling, storing, printing, or transmitting information in medical imaging. In certain examples, DICOM includes a file and data format definition for medical imaging objects and a network communications and exchange protocol. The communication protocol can include an application protocol that uses TCP/IP to communicate between systems. DICOM files can be exchanged between entities capable of receiving image and patient data in DICOM format.

HL7 is an organization involved in the development of international healthcare standards. The name HL7 is a reference to the seventh application layer of the Open System Interconnection (OSI) model, the highest level where applications communicate with each other. HL7 version 2 defines a series of electronic messages to support administrative, logistical, financial as well as clinical processes. HL7 version 2 has been updated regularly since 1987, resulting in versions 2.1, 2.2, 2.3, 2.3.1, 2.4, 2.5, 2.5.1, and 2.6. Collectively, these versions are known as HL7 version 2.x. Each HL7 v2.x standard is backwards compatible (e.g., a message based on HL7 v2.3 is understood by an application that supports HL7 v2.6). HL7 v2.x uses a textual, non-XML encoding syntax based on delimiters, and can allow interoperability between different electronic healthcare systems, such as Patient Administration Systems (PAS), Electronic Practice Management (EPM) systems, Laboratory Information Systems (LIS), Dietary, Pharmacy and Billing systems, or Electronic Medical Record (EMR) or Electronic Health Record (EHR) systems.

Other examples of medical standards include Integrating the Healthcare Enterprise (IHE), The International Classification of Diseases, 9$^{th}$ Revision (ICD-9), or Continuing Professional Education (CPE).

In addition to supporting medical standards, all commercialized medical applications used in the United States are regulated by the US Food and Drug Administration (FDA) under medical device guidelines as set by federal regulations, such as 21 C.F.R. §820 (2009). Similar regulatory bodies exist for the development and marketing of medical device products in other markets, including countries of the European Union (e.g., UK, Germany, France, Netherlands, Spain, Belgium, Portugal, and Czech Republic), Japan, India, China, South Korea, Australia, and New Zealand. These guidelines are intended to require medical application vendors to implement a quality control system and processes that includes product development (e.g., design controls), labeling, and proper investigation and handling of defects (e.g., complaints, corrective action, preventative action, etc.).

Many US and foreign regulatory bodies also endorse other quality standards, such as ISO 13485, ANSI/AAMI HE74-2001, ANSI/AAMI/ISO 14971, ASTM E1384-07, ASTM E1578, FDA General Principles of Software Validation—Final Guidance for Industry and FDA Staff, IEC 60601-1-1, IEC 62304, ISO 9001:2008, ISO/IEC 12207: 2008, ISO/IEC 15026, ISO/IEC 15288:2008, ISO/IEC 27002:2005, ISO/IEC 90003, ISO 9001:200, etc. Many quality standards require that medical applications be tested and validated for their intended use, and that the medical applications be free of defects that can cause harm to patients in their use. In certain examples, compliance is required for both pre-market and post-market approved products. For example, if a product regulated by the FDA has a defect, then the FDA can order the vendor to fix the problem, or the FDA can order the vendor to recall the product and curtail imports until the defect is fixed.

Conventional medical applications are structured in several ways. In a first example, the conventional medical application can be provided as a stand-alone hardware or software product for installation on a client computer at a healthcare site. In this example, the medical application as an executable (.exe) or a set of dynamically linked libraries (.dll) is installed on a dedicated general purpose operating system (e.g. Linux, Microsoft WindowsXP, Microsoft Windows 7, IBM Advanced Interactive eXecutive (AIX), etc.) running on the client computer and interfacing directly with resources (e.g., a physical network interface) of the client computer. Installation begins with a computer having a general-purpose operating system. To build the medical application, a medical application installation process(es) moves files from the installation environment to the disk storage system of the computer system. In addition, the installer processes normally builds a database management system (e.g., Microsoft SQL Server, Oracle, PostgreSQL (Postgres), MySQL, or others) and initializes the database management system using SQL build statements, typically inserting schema, configuration or customer specific data. In certain examples, the install process can also make registry entries or modifications through either regedit or direct editing and replacement of registration entries. When the installation is complete, the system can be tested as a part of the quality assurance and control processes. The environment provided by the client application, or any medical standard parameters (e.g., DICOM Application Entity Titles, TCP/IP addresses and ports, DICOM parameters, etc.), can be configured prior to use.

In a second example, the conventional medical application can be provided for use in a client-server architecture. In this example, a portion of the medical application is installed on a dedicated general purpose operating system (e.g., Linux, Microsoft Windows Server, IBM AIX, etc.) with server management software (e.g., Apache/Tomcat, JBOSS, IIS/ASP etc.) running on at least one server, and another portion of the medical application is installed on one or more client computers. Similar to the stand-alone medical application, the conventional client-server based medical application can be executed within the environment provided by the general-purpose operating systems of the server and client computers and can interface directly with the resources provided by the server and client computers. The installation process in this second example is similar to the first. In certain examples, client computers include installed .exe or .dll files that provide a graphical user interface (GUI) specific to the medical application. The GUI can also provide some bi-directional medical data interface (e.g., Open Database Connectivity (ODBC), Distributed Component Object Model (DCOM), Component Object Model (COM), Simple Object Access Protocol (SOAP), etc.) between the client and server computers. These processes can be repeated for each instance of the medical application installed on the client and server computers.

Either of these first or second examples can be extended to include multi-tenant situations where a medical application accesses one or more remote databases or patient data sources at one or more affiliated or unaffiliated healthcare institutions.

In a third example, the medical application can be executed as a web server application, where the medical data being acted upon is generated at one or more affiliated medical institutions. Web-server software manages user presentation, image viewing, manipulation, or processing, or response to other selectable graphical and line mode oriented input or output. The database and the network and patient data interfaces (e.g., DICOM, HL-7, or IHE-based) of the enterprise web-based environment can be similar to the server components of the client-server environment. This example can be extended to include multi-tenant situations where a medical application accesses one or more remote databases or patient data sources at one or more affiliated or unaffiliated healthcare institutions.

OVERVIEW

The present inventors have recognized, among other things, that the way software-based medical applications are currently structured have significant drawbacks. For example, each can require the medical application to be installed on a general-purpose operating system running on a computer (e.g., a client computer or a server). Installation of the medical application on the general purpose operating system is a multi-step process requiring ordinal installation of many individual software components, and in certain examples, may require a license for each installed component before the medical application is available for use, which results in a complex process, in certain examples requiring both software and human actions which can require extensive time and effort. Additionally, in certain examples, compliance with FDA requirements can result in the medical application being installed and executed on a single-user computer. Accordingly, use of the medical application can require advance preparation, and each of these ordinal processes (e.g., a specialized computer, installation, third-party licenses, etc.) can increase the overall cost and complexity of the medical application.

Further, different medical application vendors can have different proprietary software implementations of standards interfaces, which provide bi-directional transfer of medical data. Accordingly, it can be difficult to make every conventional medical application available for episodic, occasional, or non-routine usage.

Also, in certain examples, it can be difficult to monitor or control usage of the medical application once installed on the general-purpose operating system. Accordingly, medical applications are often sold for perpetual or unlimited usage, or have usage accounted retrospectively. In certain examples, unlimited usage medical application prices can range from $5,000 to over $1,000,000 per copy. In many examples, episodic or low volume usage of unlimited usage medical application is not cost effective, and, in certain examples, can discourage a healthcare site from purchasing a given medical application, effectively limiting the choices available to healthcare sites or clinicians. Healthcare sites, and more importantly, patients, can benefit from having additional medical applications available during their care. Medical applications with similar functionality can have a demonstrated difference in efficacy and specificity. The costs associated with medical applications can also hinder vendors from producing medical applications, as sales costs coupled with a finite list of customers can result in high capital acquisition purchase prices for healthcare consumers. The high cost of sales and support for advanced medical applications can hinder vendors from developing and marketing next generation applications due to a finite customer base.

In certain examples, it can be difficult to ensure security of sensitive medical data available to medical applications installed on a general-purpose operating system, or to limit access of the medical data installed on the general-purpose operating system to the client operating system, including a physical network connection. In an example, medical application providers implement multi-tenant, web-based implementations (e.g., sharing resources amongst more than one healthcare site or affiliated institution) to reduce the cost of medical applications. However, many multi-tenant or web-based implementations transfer patient outside of the healthcare facility (e.g., patient data may be sent to or stored in a third-party database), which can be particularly troublesome in healthcare settings where extra precautions must be taken to ensure privacy of patient data and compliance with regulations, such as HIPAA. In certain examples, the healthcare site is forced to rely upon relatively weak database security, such as database entries, keys, and indexes, or weak encryption practices that may result in a security breach. Moreover, in these examples, the healthcare institution(s) often must rely on the third party to maintain this security.

The present inventors have recognized, among other things, that there is a need for a mechanism to allow different medical applications from different vendors to dynamically co-exist, securely, and according to applicable regulations, on a single physical workstation, client-server, and web-server based environments. In an example, software-based medical imaging applications can be made available to clinicians on a controlled basis. Components of the system and methods are served from one or perhaps several sites connected to the Internet, or from client software in sites where healthcare is normally rendered (e.g., hospitals, medical clinics, or physician offices and/or other locations), which are also connected to the Internet. In an example, medical applications can be individually constructed into virtualized containers and made available to users through a client application, which can be installed on their computer. Once installed, the client application running on their computer can provide an interface to the medical data stored within an institution or from many institutions, provide graphical user interface processing with a user, and can provide patient data interfaces with all of the virtualized medical application containers, which are available to be run. The system and methods described herein also provide for construction of virtualized medical application containers, and mechanisms to store and download these containers.

In Example 1, a system includes one or more processors and a memory including instructions that, when executed by the one or more processors, causes the one or more processors to create a virtualized medical application container, including to create an image of a clean version of an operating system, to install a medical application on the image, and to initialize the medical application on the image.

In Example 2, the instructions that, when executed by the one or more processors, cause the one or more processors to create the virtualized medical application container of Example 1 optionally include instructions to configure the medical application to communicate with a client application on a client operating system.

In Example 3, the instructions that, when executed by the one or more processors, causes the one or more processors to initialize the medical application of any one or more of Examples 1-2 optionally include instructions to restrict access of the medical application to a network interface of the client operating system.

In Example 4, the instructions that, when executed by the one or more processors, cause the one or more processors to create the image of the clean version of the operating system of any one or more of Examples 1-3 optionally include instructions to create the operating system file system, virtual memory and cache space, kernel drivers, and bootstrap binaries.

In Example 5, the instructions that, when executed by the one or more processors, cause the one or more processors to install the medical application on the image of any one or more of Examples 1-4 optionally include instructions to install no other software on the image.

In Example 6, the memory of any one or more of Examples 1-5 optionally includes instructions that, when executed by the one or more processors, cause the one or more processors to create a copy of the virtualized medical application container, and to store the copy of the virtualized medical application container on at least one of the one or more servers.

In Example 7, the instructions that, when executed by the one or more processors, cause the one or more processors to install the medical application on the image of any one or more of Examples 1-6 optionally include instructions to install a third-party medical application executable, library, configuration file, and database management product.

In Example 8, the memory of any one or more of Examples 1-7 optionally includes instructions that, when executed by the one or more processors, cause the one or more processors to store product information about the medical application on one or more servers, wherein the product information includes at least one of a medical application name, a category, a manufacturer, a price per defined measured use, food and drug administration (FDA) clearance information, a user comment, or a user rating.

In Example 9, a machine-readable medium contains instructions that, when executed by one or more processors, cause the one or more processors to create a virtualized medical application container, including to create an image of a clean version of an operating system, to install a medical application on the image, and to initialize the medical application on the image.

In Example 10, the instructions that, when executed by the one or more processors, cause the one or more processors to create the virtualized medical application container of any one or more of Examples 1-9 optionally include instructions to configure the medical application to communicate with a client application on a client operating system.

In Example 11, the instructions that, when executed by the one or more processors, causes the one or more processors to initialize the medical application of any one or more of Examples 1-10 optionally include instructions to restrict access of the medical application to a network interface of the client operating system.

In Example 12, the instructions that, when executed by the one or more processors, cause the one or more processors to create the image of the clean version of the operating system of any one or more of Examples 1-11 optionally include instructions to create the operating system file system, virtual memory and cache space, kernel drivers, and bootstrap binaries.

In Example 13, the instructions that, when executed by the one or more processors, cause the one or more processors to install the medical application on the image of any one or more of Examples 1-12 optionally include instructions to install no other software on the image.

In Example 14, the machine-readable medium of any one or more of Examples 1-13 optionally contains instructions that, when executed by the one or more processors, cause the one or more processors to create a copy of the virtualized medical application container and to store the copy of the virtualized medical application container on at least one of the one or more servers.

In Example 15, the instructions that, when executed by the one or more processors, cause the one or more processors to install the medical application on the image of any one or more of Examples 1-14 optionally include instructions to install a third-party medical application executable, library, configuration file, and database management product.

In Example 16, the machine-readable medium of any one or more of Examples 1-15 optionally contains instructions that, when executed by the one or more processors, cause the one or more processors to store product information about the medical application on one or more servers, wherein the product information includes at least one of a medical application name, a category, a manufacturer, a price per defined measured use, food and drug administration (FDA) clearance information, a user comment, or a user rating.

In Example 17, a method includes creating a virtualized medical application container, including creating an image of a clean version of an operating system, installing a medical application on the image, and initializing the medical application on the image.

In Example 18, the creating the virtualized medical application container of any one or more of Examples 1-17 optionally includes configuring the medical application to communicate with a client application on a client operating system.

In Example 19, the initializing the medical application of any one or more of Examples 1-18 optionally includes restricting access of the medical application to a network interface of the client operating system.

In Example 20, the creating the image of the clean version of the operating system of any one or more of Examples 1-19 optionally includes creating the operating system file system, virtual memory and cache space, kernel drivers, and bootstrap binaries.

In Example 21, the installing the medical application on the image of any one or more of Examples 1-20 optionally includes installing no other software on the image.

In Example 22, any one or more of Examples 1-21 optionally include creating a copy of the virtualized medical application container and storing the copy of the virtualized medical application container on at least one of the one or more servers.

In Example 23, the installing the medical application on the image of any one or more of Examples 1-22 optionally includes installing a third-party medical application executable, library, configuration file, and database management product.

In Example 24, any one or more of the Examples of 1-23 optionally include storing product information about the medical application on one or more servers, wherein the product information includes at least one of a medical application name, a category, a manufacturer, a price per defined measured use, food and drug administration (FDA) clearance information, a user comment, or a user rating.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present inventors have recognized, among other things, a system or method for providing a controlled, per-use medical application for processing medical data in a healthcare environment, enabling a healthcare provider to improve patient outcome by providing efficient access to one or more medical applications.

In certain examples, the one or more medical applications can be made available from one or more location to one or more client computer(s) at a healthcare site (e.g., a hospital, a medical clinic, a clinician's office, etc.). In an example, usage of each medical application, or a group of medical applications, can be controlled on a real-time basis. In an example, usage can be controlled using one or more permissions satisfied prior to execution of the medical application. In certain examples, the one or more permissions can be satisfied by securing payment for a specified number of uses, for a specified period of use, for use of a particular set of patient data, or one or more combinations.

In an example, resources (e.g., a physical network interface) used by each medical application on the client computer can be controlled by a single client application, such as to increase efficiency or ensure interoperability among a plurality of medical applications. In certain examples, virtualization of the medical application can allow for download and execution, such as on a controlled-usage or limited access basis, without requiring time-consuming installation on the general-purpose operating system.

In an example, downloading and executing a virtual medical application (e.g., as a virtual appliance, as virtual software, etc.) can ensure use of the most updated version of the medical application, and, in certain examples, can help to ensure continued compliance with various informatics standards or regulatory body requirements.

Figure 1:
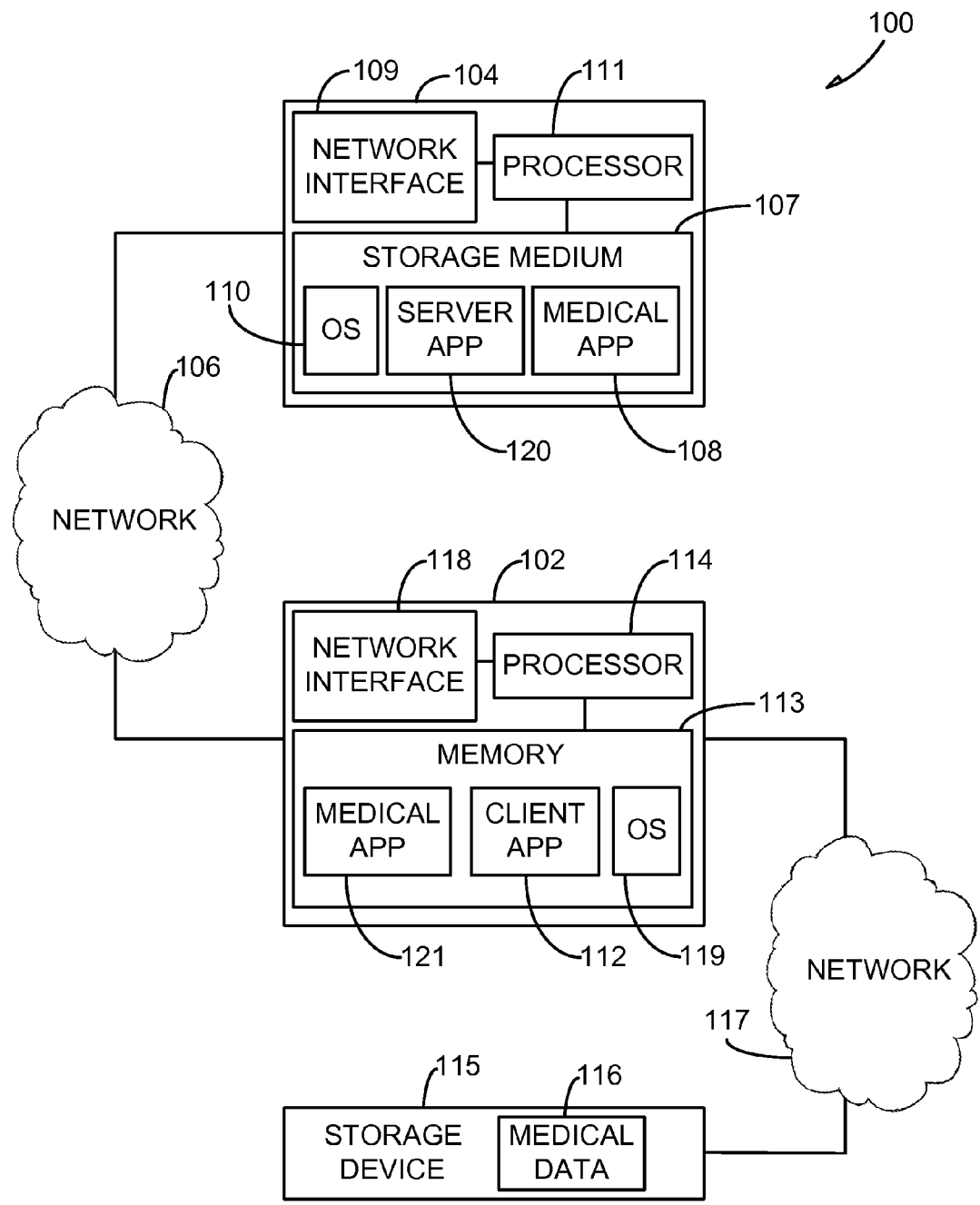
FIG. 1 illustrates generally an example of a system for processing medical data.

FIG. 1 illustrates generally an example of a system 100 configured to process medical data using one or more medical applications, including a client computer 102 having a client application 112 configured to control access of one or more medical applications (e.g., a medical application 121) to one or more client computer resources, such as a network interface 118.

In an example, the client computer 102 can include one or more client computers, client workstations (e.g., clinician workstations), or one or more other computers configured to process medical data. In an example, the client application 112 can be configured to communicate over a network 106 with a server 104 having one or more medical applications, such as the medical application 108. Further, the client application 112 can be configured to receive information (e.g., medical data 116) from a storage device 115, such as a database coupled to the client computer 102 (e.g., using a local area network, a wide area network, etc.). In an example, the client computer 102 can include a medical application 121, such as at least partially received (e.g., downloaded) from the server 104, etc. In certain examples, the client computer can include a plurality of medical applications at least partially received (e.g., downloaded) from the server 104.

In an example, the client application 112 can be configured to provide information to one or more medical applications stored at least partially on the client computer 102, and to control access of one or more of the medical applications 121 to one or more client computer resources, such as a network interface 118. In an example, the server 104 can include a processor 111 (e.g., one or more processors) coupled to a storage medium 107 (e.g., one or more hard drives, an array of hard drives, etc.). In an example, the storage medium 107 can include a general-purpose server operating system 110 (e.g., Linux, Microsoft Windows Server, IBM Advanced Interactive eXecutive (AIX), etc.)

stored or installed thereon. In certain examples, the server operating system 110 can manage one or more server software processes, and can include commercial or open source software, such as Apache/Tomcat, JBOSS, or IIS, or others to manage server-based processes. In an example, the server 104 can include a physical network interface 109 coupled to the network 106 for communication with the client computer 102.

In an example, the client computer 102 can include an operating system 119 (e.g., a general purpose operating system) stored or installed in a memory 113 and configured to be executed on a processor 114 coupled to the memory 113. The client operating system 119 can include, for example, Microsoft Windows 7, Microsoft Windows XP, Linux, Redhat, Ubuntu, Apple OS X, Google Android, Apple ITunes, or one or more other client operating systems. In certain examples, the client computer 102 can be coupled to a storage device 115, such as via a local area network 117. In an example, the external storage device 115 can include a remote server, such as via a wide area network, and can include medical data 116 stored thereon. In an example, the external storage device 115 can include a database of medical data, a medical imaging archive, clinical informatics storage, a laboratory/pathology system, an imaging modality, or other clinical users and information resources.

In an example, a physical network interface 118 can be coupled to the processor 114. In certain examples, the physical network interface 118 can be configured to couple the client computer 102 to the network 106, such as for communication with server 104. In an example, the physical network interface 118 can couple the client computer 102 to the network 117, such as for communication with the external storage device 115. In an example, the operating system 119 can include one or more client operating system resources, such as a network interface. In an example, the operating system 119 can include a resource configured to control access to the physical network interface 118.

In an example, the client computer 102 can include a client workstation running a Windows based, or other, operating system, a medical device (e.g., a magnetic resonance imaging (MRI) scanner) including a general purpose processor or memory, a mobile device (e.g., a laptop), an etc. In certain examples, the client computer 102 can include one or more inputs (e.g., keyboard, mouse, etc.) configured to receive user requests, such as a user request for a specific medical application, a user request to process data on a medical application, account information, etc.

In an example, the storage medium 107 on the server 104 can include one or more medical applications (e.g., a medical application 108) stored thereon.

In an example, the medical application 108 can include a software application or executable configured to perform one or more actions on information, such as one or more items of medical data.

In an example, the information can include one or more medical images, information about one or more medical images, healthcare information, or other medical information for a wide range of specialties, such as radiology, cardiology, urology, pathology, immunology, anesthesiology, orthopedics, genetics, dermatology, endocrinology, gastroenterology, oncology, hematology, nephrology, rheumatology, neurology, ophthalmology, surgery, otolaryngology, and psychiatry. In an example, the medical application 108 can be used by a clinician for patient diagnosis, treatment planning, post-procedure follow-up, for reporting of healthcare information in a wide variety of settings, including hospitals, clinics, laboratories, acute or long-term care facilities, rehabilitation centers, drug stores, medical imaging centers, physician offices, physicians homes, etc., or for one or more other purposes.

In an example, medical images 116 can include patient data generated through one or more diagnostic medical imaging procedures, such as x-ray, magnetic resonance imaging (MRI), ultrasound, nuclear medicine, single photon emission computed tomography (SPECT), positron emission tomography (PET), computed tomography (CT), mammography, investigative radiological sciences, endoscopy, medical thermography, medical photography, fluoroscopy, laboratory, microscopy (e.g., for human pathological investigations), elastography, optical coherence tomography (OCT), near infrared optical imaging (NIR), etc. In certain examples, medical images 116 can include patient data generated through measurement or recording techniques that produce data susceptible to be represented as maps (e.g., containing positional information), such as electroencephalography (EEG), magnetoencephalography (MEG), electrocardiography (EKG), spectroscopy, and others.

In an example, healthcare information can include information used in healthcare informatics, such as healthcare or patient related data, examination results, or knowledge. In certain examples, healthcare information can include information used in supporting aspects of diagnostics, research, and administration of clinical practices.

In an example, the medical application 108 can include medical device software, clinical or departmental solutions, enterprise-wide solutions, medical practice management, IT infrastructure solutions, electronic health records (EHR) solutions, electronic medical records (EMR) solutions, or one or more other medical application.

Medical applications 108 can be configured to assist clinicians in the diagnostic process, such as by providing information not otherwise readily available. In an example, medical device software can include computer aided diagnostic software, such as Second Look Digital from iCAD, Inc., configured to identify areas of abnormal breast tissue for further evaluation using mammography images, Neuroquant from CorTechs Lab, Inc., configured to correlate structural brain volume to normative values using MRI data, or CAD-COLON from im3D, configured to aid in evaluating suspect polyps in the colon and rectum using CT.

In an example, clinical or departmental medical applications 108 can include solutions for picture archiving and communication systems (PACS), radiology information systems (RIS), cardiology, cardiovascular information systems (CVIS), emergency department information systems, genetic reporting, laboratories, pharmacies, or one or more other solution. In an example, clinical or departmental solutions can include Centricity from General Electric Corporation, a PACS system, Horizon Cardiology CVIS from McKesson configured to provide a cardiology based departmental patient management and workflow system, or GeneInsight from Partners Healthcare System, configured to provide genetic testing report generation capabilities.

In an example, EHR or EMR solutions can include software for integrating information about a patient, including medical history, test results, diagnosis, treatments, medications, allergies, etc. EHR or EMR solutions can enable EHRs or EMRs to be accessed and modified by users across a hospital or healthcare system, as well as by authorized external partners, providing people involved in a patient's care with up-to-date information to speed up treatment or to enhance patient safety. In an example, EHR or EMR solutions can include Cerner Millennium from Cerner Corp., Meditech 6.0 from Meditech, AthenaHealth, Allscripts, Eclypsis, Epic, eClincal, or others.

In an example, the client computer 102 can include the client application 112 stored on the memory 113 and configured to initiate and control the execution of one or more medical applications, such as the medical application 108. In other examples, the client application 112 can include an executable image. In another example, the client application 112 can include one or many binary libraries or intermediate library objects controlled by a higher-level executable image. The client application 112 can communicate with a server application 120 for download or control of the medical application 108 as discussed in more detail below.

Although FIG. 1 illustrates the client computer 102 as a single client computer, in other examples, multiple client computers can be coupled to the server 104 over the network 106. Accordingly, because the client computer 102 can include multiple client computers having an instance of the client application 112 executing thereon, multiple instances of the client application 112 can communicate simultaneously with server application 120. Additionally, although the server 104 illustrated in FIG. 1 includes a single server, in certain examples, the server 104 can include a distributed server, and can include multiple sites having synchronized databases coupled to the network 106.

In an example, a medical application vendor can be provided access to the storage medium 107. Accordingly, the vendor can provide updated versions and perform other maintenance related to the medical application 108. In an example, the server 104 (or one or more other servers) can support a website for potential clients to create an account, to view available medical applications for download or use, to provide accounting information for purchase of one or more of the available medical applications (e.g., purchase tokens, establish credit, etc.), or to provide an image of the client application 112 for download to or installation on the client computer 102.

In an example, the client application 112 can communicate with the server application 120 for download or control of the medical application 108, as discussed in more detail below. In an example, communication between the client application 112 and the server application 120 can be asynchronous. One or more of these communications can be implemented using, for example, representation state transfer (REST).

In an example, the server application 120 can implement pointers or one or more tables for file system addresses for the medical application 108 stored on the storage medium 107. In an example, the server application 120 can issue approvals/denials for services to the client application 112 based upon programmable business rules. In an example, the server application 120 can issue tokens to the client application 112, authorizing use of a particular medical application on the client computer 102 (e.g., the medical application 112). In other examples, one or more other payment can be accepted or received. In an example, the server application 120 can perform transaction logging to maintain records of payments for the medical applications. Additionally, the server application 120 can maintain a database system (e.g., Microsoft SQL Server, Oracle, Postgres, MySQL, or others) to maintain customer information, medical application information, or other information. In an example, customer information can include, among others, registration information, medical applications usage history, and accounting information. Further, medical application information can include vendor data, medical application cost information, licensing mechanics, or one or more other types of information.

In an example, the medical application 108 can include a virtualized application configured to be executed on a virtual platform. In an example, the medical application 108 can include a software application that is fully installed within a container file that includes a complete run-time environment for the application. The container can include a virtualized operating system having a conventional medical application installed thereon, including an application .exe and .dll components, along with other related services including a database management system. In an example, the medical application 108 can include a VMWare, CITRIX, or other equivalent based construct or virtual operating system.

Figure 2:
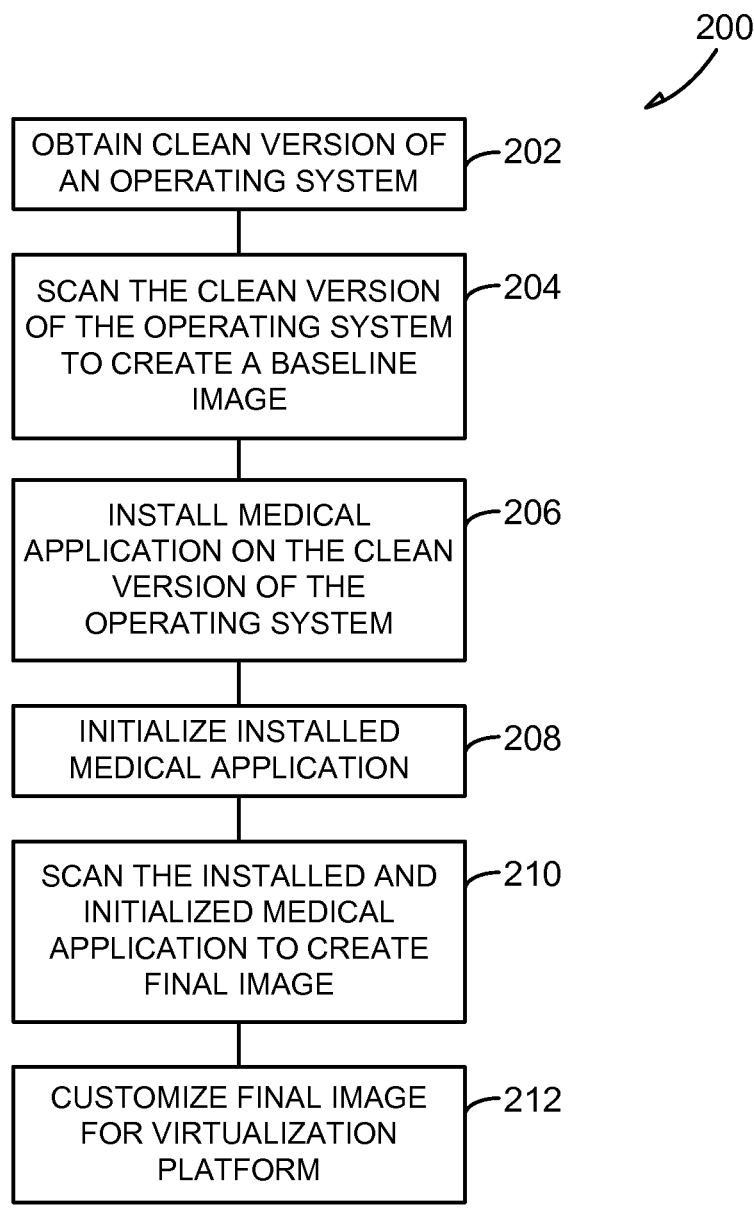
FIG. 2 illustrates generally an example of a method for forming a virtualized medical application.

FIG. 2 illustrates generally an example of a method 200 for capturing a software application for conversion into a virtualized medical application (e.g., the medical application 108, etc.). At 202, a clean version of an operation system for running the software application is obtained. The clean version of the operating system can comprise an installation of the operating system including a file system, virtual memory and cache space, kernel drivers, bootstrap binaries, and other components typically present in an installed operating system. In an example, the clean version of the operating system contains no software components in addition to those of the operating system.

At 204, a scan of a clean version of the operation is made to create and save a baseline image. The scan of the clean version of the operating system can be performed by commercially available virtualization software (e.g., VMWare, CITRIX, or others).

At 206, the software application to be virtualized is installed on the clean version of the operating system. Installation of the software application includes adding files to the operating system, such as the .exe or .dll files, the .ini or other configuration files, a data base management system product (e.g., SQLite, Postgres, or Oracle), etc.

At 208, the installed software application is properly configured and initialized. In an example, the software application can be initialized by construction of databases and tables, and input of configuration information. In certain examples, the installed software application can be configured to work directly with the client application. In other examples, the installed software application can be isolated from the environment external to the client application. In certain examples, medical data standards present within the medical application installed on the client computer can be isolated from the external environment, such that they can still be used by the internal processes of the software application, but interface with the client application to accomplish data exchange external to the installed software application.

In an example, the software application to be virtualized can make use of specified application programming interfaces (APIs) to deconstruct and/or construct input and/or output files or messages for transfer of medical data between a software application (e.g., the medical application 121) and a client application. The APIs can reference specific directories in the operating system on the client computer to accommodate the file exchange, or can be based upon TCP/IP port communications or other application-to-application communication interface methods. In an example, the specific directories can be constructed during installation of the client application on the client computer.

At 210, a scan of the configured and operational operating system and software application components thereon is then made to create and save a final image. The scan can be performed by commercially available virtualization software (e.g., VMWare, CITRIX, or others), which access the differences between the initial baseline image and the final image. The resultant difference can include an executable file.

At 212, the executable file compression, sandbox location, and domain user access to applications is customized according to the virtualization platform used (e.g., VMWare, CITRIX, or others). The executable file can then go through a final build process to form the completed virtualized application. Once formed, the virtualized medical application can be stored in memory on the server.

Advantageously, virtualization of the medical application can enable quick and easy use of heterogeneous medical applications at a client computer. Because the medical applications are virtualized, it is efficient for a user to use a medical application a single (or small number) of times, because the user is not required to install the medical application on the operating system of the client computer. Instead, the virtualized medical application includes the operating system files necessary for operation therewith. Additionally, the containerization process of the virtualized software application can enable restrictions or controls on the software application. Furthermore, because the medical application is not directly installed in the operating system, the client application can more easily control the initial execution of the medical application.

In an example, the client application (e.g., the client application 112) can control one or more medical applications by providing an interface between one or more medical applications and one or more resources of the client computer.

In an example, a medical application (e.g., the medical application 121) can interact with the client application, and the client application can act as the interface between the medical application and resources of the client computer (e.g., the client computer 102). In an example, because each medical application (e.g., the medical application 108, 121) is configured for use on a virtual platform, all instances of a medical application on disparate computers can be identical. In an example, the medical application does not have to be individually configured for each computer, because the virtual platform and client application with which the medical application interacts is identical on all computers. In an example, a single copy of a medical application (e.g., the medical application 108, 121, etc.) can be run on multiple disparate computers.

Moreover, the client application can be configured to perform services to support one or more medical standards used by the one or more medical applications. In an example, the client application can perform services including maintaining databases and interfacing with external sources of medical data (e.g., the medical data 116). Accordingly, the medical application does not need to be configured for the services provided by the client application. Instead, the medical application can be configured to communicate with the client application, and the client application can perform the services for the medical application. In an example, this can improve efficiency of executing multiple medical applications on a single computer, because the medical application does not maintain separate services for a given medical standard. In an example, each of the medical applications (e.g., medical application 108, 121) can interface with the client application, and the client application itself can provide a common set of services to support the one or more medical standards. Additionally, because the client application can perform the services, in certain examples, the client application can be configured for site-specific parameters only. Moreover, because the client application can be configured for site-specific parameters, in certain examples, the medical application is not required to be specifically configured to the site. Accordingly, in certain examples, the configuration for site-specific parameters can occur on only the client application, and one or more medical applications (e.g., the medical application 121, etc.) can be executed based on this configuration.

In an example, one or more databases provided by the client application for support of one or more medical standards can be used for storage of medical data. For example, after a medical application has executed and generated results, the results can be stored in the database of the client application. Thus, the user can access the results even when the medical application is not currently executing. Accordingly, even if the client application does not allow execution of the medical application (e.g., because the appropriate token not present), the results from a previous execution can still be accessed. In an example, the database can include a database (e.g., Microsoft SQL Server, Oracle, Postgres, MySQL, or others). In an example, the client application can provide services for one or more medical standards for encoding, storage, exchange, and decoding of medical data, such as DICOM, HL-7, IHE, ICD, CPE, etc.

Figure 3:
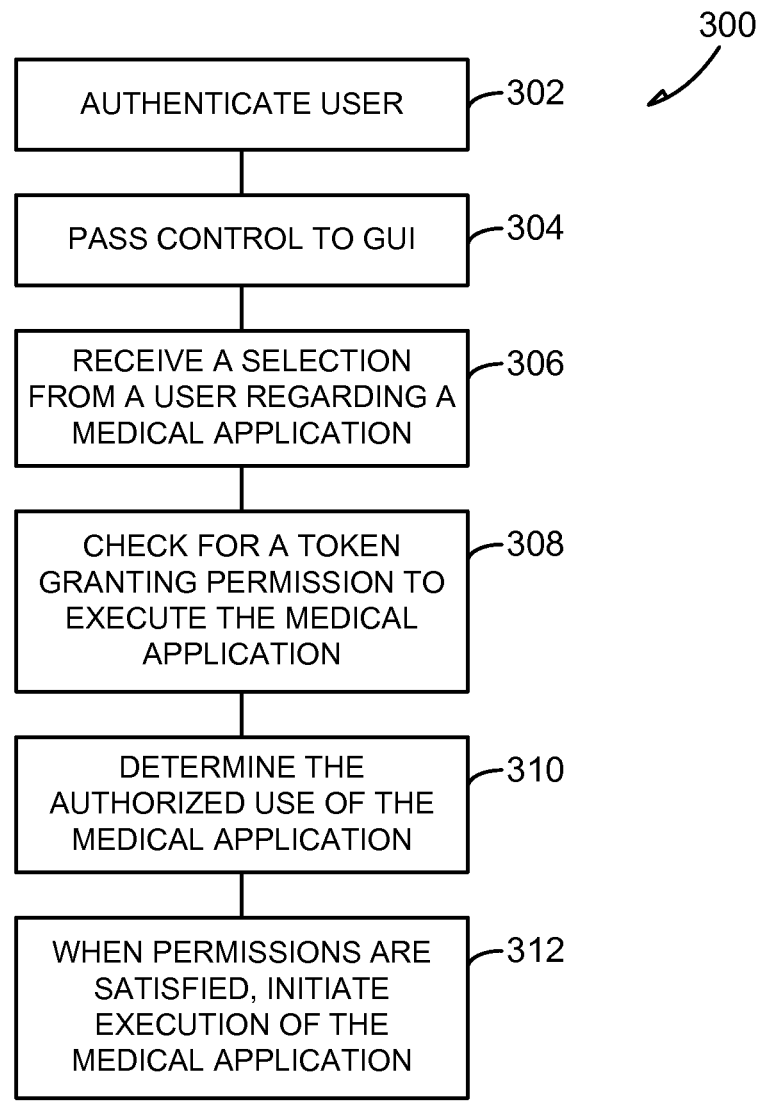
FIG. 3 illustrates generally an example of a method for executing a medical application.

FIG. 3 illustrates generally an example of a method 300 for controlling execution of a medical application. At 302, the client application authenticates a user of the client application. To authenticate the user, the client application is initiated on the client computer and the client application requests user information, such as a username and password, etc. The client application can authenticate the user information against either a local or networked authentication directory, or file, or service. Login attempts can be stored at one or both of a client transaction log on a client computer (e.g., the client computer 102) or a client transaction log on a server (e.g., the server 104). The user information can provide the client application with the identity of the user.

At 304, after authentication of the user, the client application can pass programmatic control to a graphical user interface (GUI) of the client application. In certain examples, the GUI can provide interaction with a user of a client computer (e.g., the client computer 102). In an example, the GUI can perform functions including providing a display and manipulation of medical data (e.g., patient demographic, clinical, or imaging data) that is stored within a database or file system provided by the client application, providing a listing of the names of medical applications stored in the database of the client application, providing a listing of the names of medical applications available for use on the server or website, and other client application graphical user elements.

At 306, the client application receives a selection of a medical application from the user. In an example, the user can select one or more of the medical applications using an input device coupled to the client computer. In another example, the medical applications may automatically be selected for use based upon a pre-determined set of algorithms and tables, which will either choose one or more medical applications and specific patient data to run in sequence. The user may also select a patient data set for the client application (e.g., the client application 112) to process as input.

At 308, the client application checks for a token or other information (e.g., credit, license, etc.) granting permission to execute the medical application. In an example, the token can include a software token that is unique number used as a security device for authentication of the medical application. In an example, the token can be generated by the server. In other examples, the token can include one or more other indications of credit, good standing, license, etc. After receiving a selection of the medical application from the user, the client application can send a request to the server for a token for the medical application. In an example, the request for the token that is sent to the server can include specific patient information to be processed by the medical application, a timestamp, an identification of the user of the client application, or an amount of usage (e.g., length of time) requested for the medical application. In an example, the request can include a REST-based message that is either secure or non-secured.

In certain examples, the server can determine whether a payment has been secured for the medical application use to process a specific set of patient data. In an example, usage can be metered, and the server can determine if an adequate cash or credit balance exists, or other rights which have been granted to pay for the amount of usage requested. When payment has been secured, the server can determine what type of license to grant. In an example, the server can grant a license for a single use, a defined number of uses, or unlimited uses. In another example, the server can grant a license for an unlimited number of uses, but limited to use on a specific set of medical data. In yet another example, the server can grant a license for a defined length of time (e.g., 24 hours), or a specified number of uses in a defined length of time, etc. When the server has verified that payment has been secured for the medical application, the server can generate a token with the appropriate license and send the token to the client application on the client computer. In an example, the token can be used to grant the permissions by including an identification of the patient or patient data upon which use is authorized. In another example, the token can be used to grant the permissions by including identification of the medical application for which use is authorized, or can include both. In other examples, the token permissions can be based on the creation (input) or dissemination (output) of medical data supplied to, for example, a web-based multi-tenant application (e.g., such as described in more detail with respect to FIG. 5). In an example, the token can be sent to the client application in a REST-based message that is either secure or non-secured.

At 310, the client application can determine the authorized use of the medical application based on the permissions provided by the token for the medical application. Having token-based use of the medical application can provide several advantages. For example, token-based use can enable the client application to ensure payment has been secured prior to use of the medical application. Additionally, tokens can provide a simple mechanism enabling the client application to control use a medical application. In other examples, other forms of permission or authorization different than tokens can be used.

At 312, when all of the permissions of the token are satisfied, the client application can initiate execution of the medical application. In an example, the token can be stored by the client application on the client computer. Thus, the token does not need to be downloaded to be re-used for usage of the same medical application and patient data. In another example, the token can be deleted after use (e.g., automatically), and a new instance of the medical application (e.g., or another copy) can be obtained from the server to authorize future use.

In an example, when initiating the execution of the medical application after the token has been sent from the server, the client application can use the token again for initiation of the execution of the medical application. The client application can re-verify each of the permissions of the token prior to execution of the medical application. As another example, if the token authorized use of the medical application for a certain time frame, the client application can verify that the time frame has not passed.

Another advantage of token-based use of the medical application is that the medical application for which the token authorizes use can be executed on disparate computers as long as the permissions of the token are satisfied. For example, the token and a link to the medical application, along with other information, can be sent by the client application from the client computer to another remote computer having another copy of the client application installed thereon. The remote copy of the client application can receive the token and the link to the medical application and additional information and execute the medical application according to the permissions of the token. In other examples, the token and the link to the medical application along with other information can be downloaded from the server by the other remote computer.

In certain examples, the medical application can be executed on the client computer, the server, or another computer (e.g., as explained in more detail below with respect to FIG. 5). Prior to use of the medical application, the client application can verify the permissions associated with the selected medical application and can initiate execution of the medical application if the permissions are satisfied.

Once the medical application has been initiated, the client application controls execution of the medical application to ensure compliance with the granted permissions and to limit the access of the medical application to resources (e.g., a network interface) of the client computer. In an example, all communications from the medical application to resources external to the client computer are accomplished through the client application. The client application can control data exchange interfacing to the local network and construct the data into a file structure that is passed between the client application and the medical application. The medical application is limited to only communicating with the client application for external communications.

In an example, the client application can periodically download a medical application (e.g., the medical application 121) for use to maintain updated versions. In another example, a server (e.g., the server 104, which can include one or more servers) can push updated versions of the medical application (e.g., the medical application 108) to the appropriate computer (e.g., the client computer 102). After an updated version of a medical application is stored in the storage medium of the server, the server can send the updated version to the appropriate computer (e.g., the client computer 102) to replace an older version of the medical application (e.g., the medical application 121) stored thereon. Advantageously, because the medical application can be configured to execute on a virtual platform, the medical application requires minimal individual configuration and minimal IT support. This enables the most current version of the medical application to be easily obtained and reduces the issue associated with using outdated or unsupported versions of the medical application. In an example, if the application is deleted from the computer, when the user selects the medical application for use the next time, the medical application can be downloaded again.

In an example, the client application can perform transfer of medical data to another client application executing on another computer. In an example, the transfer of medical data simplifies a peer-to-peer consultation (e.g., allowing multiple users to run the medical application on the particular set of medical data). Advantageously, when a token grants use to a particular medical application for a particular set of patient data, the ability to send the token and medical application to a remote computer enables peer-to-peer consulting (e.g., having multiple users run the medical application on the particular set of patient data) without requiring each user to individually secure access to the medical application. Instead, a single token can be obtained and sent to each computer for execution of the particular medical application.

In an example, the client application can include a mechanism to request or respond to a peer-to-peer consultation. In an example, the peer-to-peer consultation can be performed manually, such that a request to perform medical data transfer is manually selected via an input device on a computer. In another example, the peer-to-peer consultation can be performed through an automated administrative script bi-directional medical data transfer. In an example, when a request to perform a medical data transfer is selected, the client application can send medical data (e.g., according to the DICOM standard) to another client application. Additionally, the other client application can send medical data (e.g., results) back to the client application for viewing.

In an example, the client application can provide background processes that implement DICOM services including DICOM storage Service Class Provider (SCP) and Service Class User (SCU), DICOM query/retrieve SCU/SCP, and DICOM storage commit SCU/SCP. For non-DICOM based medical data, the client application can provide HL-7 based services. In an example, the HL-7 services can be used to exchange medical data including patient demographic, financial, and reporting data including scheduled and performed medical procedures, test results, and patient status information. In an example, the medical data can be transferred based on XML-based methods along with Simple Object Access Protocol (SOAP).

In an example, client application can also include a manual query/retrieve operation for accessing medical data. The query/retrieve operation can, for example, be based on a DICOM standard query/retrieve SCU operation. In an example, the client application can include a manual medical data storage operation. The storage operation can be based on, for example, a DICOM standard storage SCU operation. In an example, the client application can include a transmit results operation. The transmit results operation can be based on, for example, the DICOM standard. In an example, the client application can include buttons to import and export DICOM files to a CD/DVD. In an example, the client application can include buttons to search DICOM metadata.

Figure 4:
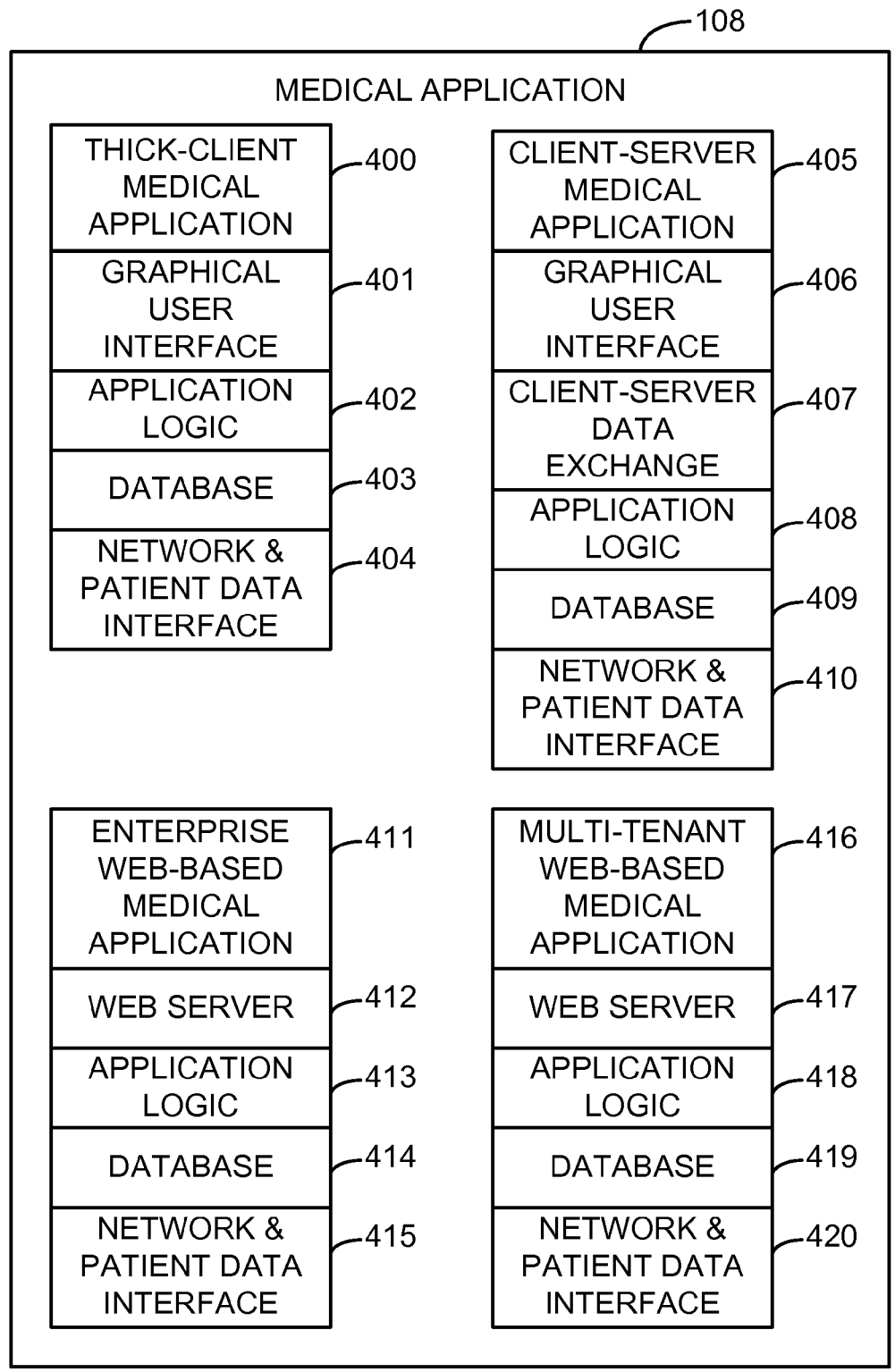
FIG. 4 illustrates generally an example of the storage and structure of one or more medical applications stored on a networked server or other storage location.

FIG. 4 illustrates generally an example of the storage and structure of one or more medical applications (e.g., a medical application 108) stored on a networked server or other storage location. In an example, the medical applications 108 can include one or more (e.g., an unlimited number) of medical applications configured to be available to a client application (e.g., the client application 112) for download or use. In certain examples, the one or more medical applications can be constructed with reference to one or more of the examples described in FIG. 2.

In an example, the client application can be configured to receive a selection (e.g., a user selection, an automated selection, etc.) of a medical application (see, e.g., step 306 of FIG. 3). If the selected medical application is not stored locally on a client computer hosting the client application, then the client application can be configured to communicate with the networked server to download a copy of the selected medical application, such as from a storage medium (e.g., the storage medium 107). In an example, the storage medium can include a medical application repository stored in a read/write computer medium, such as a magnetic disk physical file system, a memory-based file system (e.g., a virtual file system, a ram disk, etc.) or other storage medium.

In an example, the medical application (e.g., the medical application 108) can be downloaded, such as through an internet-based download software program (e.g., file transfer protocol (FTP)). Once downloaded, the medical application can be executed on the client computer. In an example, the client application can include a GUI configured to provide an indication of the download status of the medical application, and to receive user commands, such as for execution, etc. The medical application can be executed within a virtual platform provided on the client computer (e.g., such as described in step 312 of FIG. 3). In certain examples, the virtual platform can be provided by a commercial vendor, such as VMWare, CITRIX, or other comparable software.

In an example, commercial or research medical applications developed to support one or more of a thick-client (e.g., a thick-client medical application 400), client-server (e.g., a client-server medical application 405), enterprise web-based (e.g., an enterprise web-based medical application 411), or multi-tenant web-based (e.g., a multi-tenant web-based medical application 416) architectures can be virtualized, such as through processes described in FIG. 3, and can be stored on a server (e.g., the server 104) as container files, .dat files, or one or more other virtualized file structures.

In an example, a thick-client environment for execution of a medical application can include the thick-client medical application 400, a graphical user interface 401, applications logic 402, a database 403, a network and patient data interface 404, and in certain examples, additional programs or files to support customization, backup, or application security or other support functions.

In an example, the graphical user interface 401 can manage user presentation, image viewing, manipulation, or processing, or response to other selectable graphical and line mode oriented input or output. The applications logic 402 can include business rules logic, image processing, measurement, or quantification logic, or software services logic, as well as other application logic components. The database 403 can include a database server configured to support ODBC, Java Database Connectivity (JDBC), Microsoft ActiveX Data Objects (ADO), or other connections or connector methods, can include a database manager (e.g., Microsoft SQL Server, Oracle, Postgres, MySQL, or others) configured to create or delete databases, tables, elements, keys, indexes, or other components, and can be configured to provide one or more storage systems configured to either store medical or other data, or pointers including addresses of data on one or more file systems. The network and patient interface 404 can be configured to facilitate bi-directional communication (e.g., 802.xx physical network) and logical exchange of patient or other data through either proprietary or standards based methods (e.g., DICOM, HL-7, IHE).

In an example, a client-server environment for execution of a medical application can include the client-server medical application 405, a graphical user interface 406, a client-server data exchange 407, applications logic 408, a database 409, a network and patient data interface 410, and in certain examples, additional programs or files to support customization, backup, or application security or other support functions. In an example, the client-server medical application 405 can be configured to be at least partially executed on a server over a network and at least partially on a client computer. In an example, at step 208 of FIG. 2, the client application can be configured to run the graphical user interface 406, the client-server data exchange 407, the applications logic 408, the database 409, and the network and patient data interface 410, in certain examples, all in the same container file, .dat file, or one or more other virtualized file structures.

In an example, the graphical user interface 406, the applications logic 408, the database 409, and the network and patient data interface 410 of the client-server environment can be similar to the respective components of the thick-client environment. The client-server data exchange 407 can be configured to support communication between one or more remote clients and one or more servers. In certain examples, the client-server data exchange 407 can be implemented by the client application (e.g., the client application GUI) using one or more remote SQL calls to the applications logic 408 or to the database 409, by file transfer (e.g., FTP or one or more other file exchange protocols), or by proprietary data exchange methods.

In an example, an enterprise web-based environment for execution of a medical application can include an enterprise web-based medical application 411, a web server 412, applications logic 413, a database 414, a network and patient data interface 415, and in certain examples, additional programs or files to support customization, backup, or application security or other support functions. In an example, the enterprise web-based medical application 411 can be configured to be executed on a remote server (e.g., a third-party server). In an example, the run-time environment for at least a portion of the enterprise web-based medical application 411 can be provided on the remote server, which can be situated on either a local area network (LAN) or a wide area network (WAN).

The enterprise web-based medical application 411 can include a centralized image of the medical application configured to provide a user with a browser interface. In certain examples, the web-based medical application components can be virtualized (e.g., such as discussed above with respect to one or more of the steps described in the examples of FIG. 2) and downloaded to a computer (e.g., the client computer 102). In an example, the web-based medical application can provide a browser interface (e.g., HTTP, HTTPS, Flash, Silverlight, etc.) configured to provide interaction with a user at one or more network addressable computers supporting a web-browser (e.g., Internet Explorer, Safari, Firefox, Chrome, etc.). In an example, the browser interface can execute in a run-time environment within the client operating system of the client computer (e.g., the operating system 119 of the client computer 102). In an example, while web browser usage (e.g., HTTP, HTTPS, Flash, Silverlight, etc.) can be similar to web-based medical applications that may have not been virtualized, control of the web-based medical application can be asserted through the exchange of patient data using a client application (e.g., the client application 112). In certain examples, control of the web-based medical application can be asserted solely through the exchange of patient data using the client application.

In an example, the client application can control data exchange with a local network and construct the data into a file structure that is passed between the client application and the web-based medical application. In certain examples, the web-based medical application is limited to only communicating with the client application for external communications. In these examples, messages sent to or from the server are sent through the client application, and not through the web-based medical application, and patient data processed by the enterprise web-based medical application 411 is provided by the client application.

In an example, the web server 412 can manage user presentation, image viewing, manipulation, or processing, or response to other selectable graphical and line mode oriented input or output. In an example, the applications logic 413, the database 414, and the network and patient data interface 415 of the enterprise web-based environment can be similar to the respective components of the client-server environment.

In an example, a multi-tenant web-based environment for execution of a medical application can include a multi-tenant web-based medical application 416, a web server 417, applications logic 418, a database 419, and a network and patient data interface 420. In an example, the multi-tenant web-based environment can be similar to the enterprise web-based medical environment. However, in certain examples, patient data in the multi-tenant web-based environment can originate from more than one affiliated or unaffiliated medical institution. Accordingly, database record keeping can be established to support a segregated institutional view of the patient data from a multi-tenant database.

In an example, at step 312 of FIG. 3, once a token is obtained and associated permissions are satisfied, the medical application 108 can be executed. Accordingly, one or more components of the thick client environment, the client-server environment, the enterprise web-based environment, or the multi-tenant web-based environment can be executed and run on the client computer, in certain examples, different than (e.g., prior to) one or more of the steps described in the examples of FIGS. 2 and 3.

Figure 5:
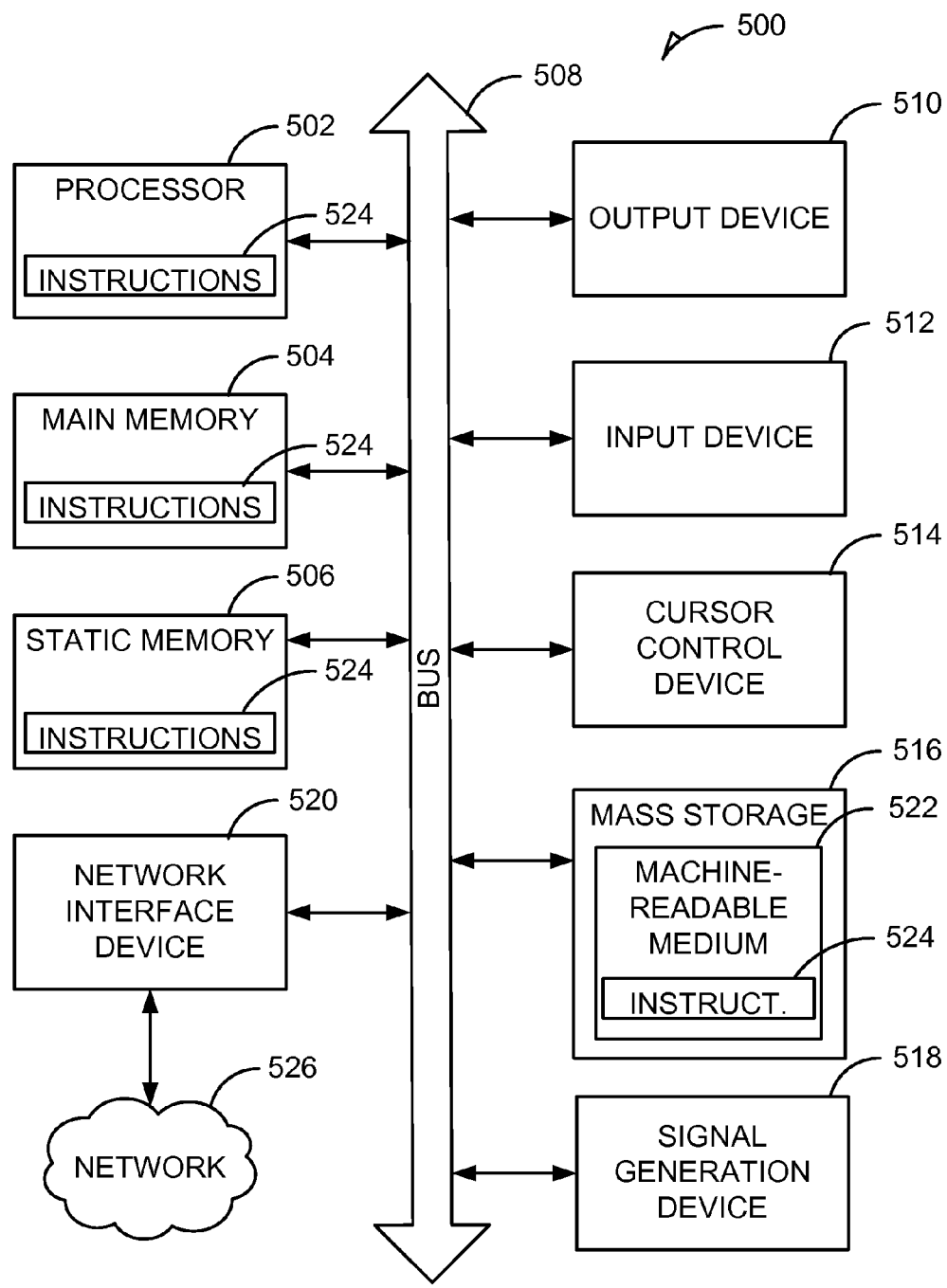
FIG. 5 illustrates generally an example of a machine for processing medical data.

FIG. 5 illustrates generally an example of a computer 500 (e.g., the client computer 102, the server 104, etc.). Upon reading and comprehending the content of this disclosure, one of ordinary skill in the art will understand the manner in which a software program can be launched from a computer-readable medium in a computer-based system to execute the functions defined in the software program. One of ordinary skill in the art will further understand the various programming languages that can be employed to create one or more software programs designed to implement and perform the methods disclosed herein. The programs can be structured in an object-orientated format using an object-oriented language, such as Java, C++, or one or more other languages. Alternatively, the programs can be structured in a procedure-orientated format using a procedural language, such as assembly, C, etc. The software components can communicate using any of a number of mechanisms well known to those of ordinary skill in the art, such as application program interfaces or inter-process communication techniques, including remote procedure calls or others. The teachings of various embodiments are not limited to any particular programming language or environment.

Thus, other embodiments can be realized. For example, an article of manufacture, such as a computer, a memory system, a magnetic or optical disk, some other storage device, or any type of electronic device or system can include one or more processors 502 coupled to a machine-readable medium 522 such as a memory (e.g., removable storage media, as well as any memory including an electrical, optical, or electromagnetic conductor) having instructions 524 stored thereon (e.g., computer program instructions), which when executed by the one or more processors 502 result in performing any of the actions described with respect to the methods above.

The computer 500 can take the form of a computer system having a processor 502 coupled to a number of components directly, and/or using a bus 508. Such components can include main memory 504, static or non-volatile memory 506, and mass storage 516. Other components coupled to the processor 502 can include an output device 510, such as a video display, an input device 512, such as a keyboard, a cursor control device 514, such as a mouse, and a signal generation device 518 (e.g., a speaker or a light emitting diode (LED)). A network interface device 520 to couple the processor 502 and other components to a network 526 can also be coupled to the bus 508. The instructions 524 can further be transmitted or received over the network 526 via the network interface device 520 utilizing any one of a number of well-known transfer protocols (e.g., HTTP). Any of these elements coupled to the bus 508 can be absent, present singly, or present in plural numbers, depending on the specific embodiment to be realized.

In an example, one or more of the processor 502, the memories 504, 506, or the storage device 516 can each include instructions 524 that, when executed, can cause the machine 500 to perform any one or more of the methods described herein. In alternative embodiments, the computer 500 operates as a standalone device or can be connected (e.g., networked) to other machines. In a networked environment, the machine 500 can operate in the capacity of a server or a client machine in server-client network environment, or as a peer machine in a peer-to-peer (or distributed) network environment. The computer 500 can include a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine 500 is illustrated, the term "machine" shall also be taken to include any collection of machines that individually or jointly execute a set (or multiple sets) of instructions to perform any one or more of the methodologies discussed herein.

While the machine-readable medium 522 is shown as a single medium, the term "machine-readable medium" should be taken to include a single medium or multiple media (e.g., a centralized or distributed database, or associated caches and servers, and or a variety of storage media, such as the processor 502 registers, memories 504, 506, and the storage device 516) that store the one or more sets of instructions 524. The term "machine-readable medium" shall also be taken to include any medium that is capable of storing, encoding or carrying a set of instructions for execution by the machine and that cause the machine to perform any one or more of the methodologies of the present invention, or that is capable of storing, encoding or carrying data structures utilized by or associated with such a set of instructions. The term "machine-readable medium" shall accordingly be taken to include, but not be limited to tangible media, such as solid-state memories, optical, and magnetic media.

Other Examples

In an example, the client application (e.g., the client application 112) can be configured to provide a virtual store of medical applications to a user for selection. In an example, a plurality of medical applications can be stored on one or more servers, and information about the plurality of medical applications can be made available to the client application for presentation to the user (e.g., using a client computer). In certain examples, the information available to the user through the virtual store can include: the medical application name; the version number; application categories (e.g., radiology, cardiology, modality, organ, etc.); price per defined measured use; manufacturer name; manufacturer contact information; customer support information; FDA clearance information (e.g., FDA cleared or approved, research only, etc.); 510(k) or premarketing approval (PMA) information (e.g., number, approval date, etc.); user comments (e.g., access to a blog, etc.); user ratings; training materials; manuals; application requirements; etc.

Further, in other examples, the client application can be configured to compare medical information (e.g., metadata in a DICOM file) to a pre-set table of medical applications to automatically suggest or provide access (e.g., using a token) to one or more medical applications compatible with the medical information. In an example, other information can be used, such as user preference, etc. If the suggested medical application is available on the client computer, the medical application can be executed. If the suggested medical application is not available, the medical application can be located and retrieved (e.g., downloaded, such as automatically).

Third-Party Medical Applications

In certain examples, the medical applications referenced herein (e.g., the medical application 108, 121, etc.) can include one or more commercially available or other medical applications.

For example, the medical application can include one or more of the following:

eFilm from Merge, a desktop DICOM viewer application;

Cadstream from Merge, a mammography CAD, prostate CAD, and liver CAD application;

Iread Mammo from Merge, a mammography viewing application;

Fusion Web from Merge, a Clinical access portal application;

Pro Planner from Cedara, an orthopedic viewing application;

Vericis from Amicas, a cardiology viewing and analysis application;

Hemodynamics from Amicas, a cardiology data collection and reporting tool;

ColonCar from Viatronix, a virtual colonoscopy application;

Cadens Colon from Cadens Imaging, a virtual colonoscopy application;

Second Look from ICAD, a mammo CAD application;

Spectralook from ICAD, a breast MRI CAD application;

Vividlook from ICAD, a prostate CAD application;

Veralook from ICAD, a virtual colonoscopy CAD application;

LMS Lung from Median Technologies, a lung lesion management application;

LMS Liver from Median Technologies, a liver lesion management application;

Softview from Riverain Medical, a bone suppression application;

Ongaurd from Riverain Medical, a chest x-ray CAD application;

Inbox from LifeImage, a universal imaging inbox e-sharing application;

Orthoview from Orthoview, an orthopedic digital templating application;

Ensite Velocity from St Jude Medical, a cardiac mapping application;

Resolution MD from Calgary Scientific, a radiology 3D viewing application;

Resolution MD Cardiac from Calgary Scientific, a calcium scoring, ventricular function, coronary analysis application;

Vitrea Cardiac from Vital Images, a cardiac imaging application;

Vitrea Vascular from Vital Images, a vascular imaging application;

Vitrea Neuro from Vital Images, a neuro imaging application;

Vitrea Oncology from Vital Images, a lung nodule analysis, tumor segmentation application;

IQQA Chest from EDDA Technologies, a DR/CR chest CAD application;

IQQA Liver from EDDA Technologies, a liver volumetric assessment and analysis application;

Clear Canvas Workstation from Clear Canvas, a DICOM viewer application;

3D Netsuite from Biotronics, a perfusion, lung, vessel & colon 3D rendering applications application;

IPlan Bold from Brainlab, a MRI brain mapping software application;

Vectorvison Spine from Brainlab, a fusion of CT and fluro images for spine surgery navigation application;

Vectorvison Truma from Brainlab, a virtual fluroscopy for fracture reduction and screw insertion application;

Unity Cardiology PACS from DR Systems, a cardiology viewing and measurement application;

CD-Colon from im-3D, a 3D colon analysis application;

Image Analysis, a Coronary calcium scoring, an aortic calcium scoring, HIP BMD, Spine BMD application;

TramaCad from Voyant Health, an orthopedic digital surgery planning application;

Pre-Operative Planning from Sectra, digital templating modules for hips, knees, and fracture repositioning application;

Illuminate from Softek, a search engine that searches for specific items in Isite PACS database;

AquariusNet from TeraRecon, a web-based 3D reconstruction application;

LesionOne from Three Palm Software, a breast lesion tracking application;

Sliceomatic from Tomovision, segmentation software for MRI imaging;

DICOmatic from Tomovision, which converts proprietary image formats to DICOM;

Ultravet from Ultrarad, a toolset for veterinary image viewing;

Visage CS from Visage, 3D imaging for cardiac, neuro, oncology;

Ziostation for Cadiology from Ziosoft, a Cardiac function analysis, coronary analysis, calcium scoring application;

Ziostation for Nuero from Ziosoft, a CT Brain perfusion, CT vessel analysis, CT subtraction application;

Ziostation for Oncology from Ziosoft, a colon analysis, image fusion, multi-data set comparison application;

Ziostation surgical planning from Ziosoft, a multi-mask fusion application;

Cardiolnsight, a cardiac mapping application;

Image-Arena from TomTec, a 2D LV & CPA—left ventricle cardiac performance analysis application;

Image-Arena from TomTec, an intra-media wall thickness analysis used for bi-ventricular lead placement application;

Image-Arena from Tom-Tec, a 4D LV—3D recon over time of the left ventricular application;

Image-Arena from Tom-Tec, a right ventricular volume analysis application;

Image-Arena from Tom-Tec, a 4D MRI LV analysis application;

Image-Arena from Tom-Tec, a 4D mitral valve analysis application;

NeuroQuant from Cortechs Labs, a Brain mapping application;

Caseplan from Stryker, a advanced pre-operative planning application;

Centricity from GE, a cardiology PACS application;

Centricity from GE, a radiology PACS application;

Centricity from GE, a woman's imaging application;

Careware from Cerner, a multi-media imaging integration application;

Mellenium from Cerner, a cardiovascular image viewing application;

Millennium from Cerner, a radiology image viewing application;

Powerworks from Cerner, a practice management application;

iSite PACS from Phillips Medical, a radiology viewing application;

CVIS from Phillips Medical, a cardiovascular information and viewing application;

iSite Volume Vision from Phillips Medical, a 3D image recon and analysis application;

IMAnalytics Workspace from Phillips Medical, an advanced image analysis quantification and visualization tool kit application;

CoPathPlus from Sunquest, a digital pathology application;

Webpax, a DICOM viewer application;

Scanscope from Aprerio, a pathology viewing application;

Virtuoso from Bioimagene, a pathology viewing application;

Alphelion from ADICS, 3D Image processing and viewing for pathology;

PathPacs from Apollo, a pathology PACS application;

CareEnhance CAD from McKesson, a CAD application for coronary artery disease application;

Horizon CVIS from McKesson, a cardiology management system application;

Horizon Cardiology Web from McKesson, a web-based cardiology imaging application;

Horizon Lab from McKesson, a pathology application;

Horizon Practice Analytics from McKesson, a practice analytics application;

Radiology Office from McKesson, a RIS/PACS solutions application;

Syngo InSpaceEP from Siemens, 3D cardiac viewing and segmentation application;

Syngo Dynamic PET from Siemens, a myocardial perfusion application;

Sygno RT Physicist from Siemens, imaging and advanced data processing for radiology imaging;

Syngo MulitModality Workspace from Siemens, a workspace for viewing images from multiple sources application;

Perfit from Hermes Medical, a cardiac perfusion analysis application;

Image Fusion from Hermes Medical, a multimodality image fusion and co-registration application;

Lung Volume from Hermes Medical, a lung analysis application;

Kidney Analysis from Hermes Medical, a kidney imaging and analysis application;

3D Imaging software from USC, 3D imaging and analysis software for urology; or

Volume 4D Pro from ScienceGL, a 4D MRI and CT voxel data analysis application.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

What is claimed is:

1. A computing system comprising:
   at least one processor; and
   a memory including instructions to implement a client application that, when executed by the at least one processor, causes the at least one processor to perform electronic operations that:
   control access of a medical application to a resource of a client operating system operating on the computing system;
   receive medical data from a data source that is external to the client application and the medical application;
   provide information to the medical application based on the received medical data; and
   control execution of the medical application and control access to the received medical data, to comply with at least one patient data privacy requirement defined by medical informatics standards or medical informatics regulations;
   wherein the client application is provided to computing system as a container that is deployable in the client operating system;
   wherein the container provides a virtualized operating system for operation of the medical application and the client application, wherein the virtualized operating system executes within the client operating system, and wherein the virtualized operating system is separated from the client operating system; and
   wherein the client application and the medical application operate in the virtualized operating system, and wherein the client application and the medical application operate without installation of the client application and the medical application onto the client operating system.

2. The system of claim 1, wherein the electronic operations that receive the medical data include electronic operations to:
   receive medical data according to information communication characteristics defined by a first medical standard.

3. The system of claim 1, wherein the instructions to implement the client application, when executed by the at least one processor, cause the at least one processor to perform further electronic operations that:
   control access to the medical application.

4. The system of claim 1, wherein the instructions to implement the client application, when executed by the at least one processor, cause the at least one processor to perform further electronic operations that:
   receive an indication of a request for metered use of the medical application;
   request permission for metered use of the medical application, wherein the metered use includes at least one of a single use, a defined number of uses, unlimited use, or timed use;
   receive at least a portion of the medical application in response to the request for metered permission; and
   execute at least a portion of the medical application.

5. The system of claim 1, wherein at least a portion of the medical application includes a virtualized medical application; and
   wherein the instructions to implement the client application, when executed by the at least one processor, cause the at least one processor to perform further electronic operations that:
   control access of the virtualized medical application to the resource of the client operating system; and
   provide information to the virtualized medical application based on the received medical data.

6. The system of claim 1, wherein at least a portion of the medical application includes a virtualized medical application operable in the virtualized operating system;
   wherein the memory further includes instructions to implement the virtualized medical application that, when executed by the at least one processor, causes the at least one processor to perform further electronic operations that:

receive information provided by the client application using based on the received medical data; and process the received information.

7. The system of claim 1, wherein at least a portion of the medical application includes a web-based medical application; and wherein the instructions to implement the client application, when executed by the at least one processor, cause the at least one processor to perform further electronic operations that:

control access of the web-based medical application to the resource of the client operating system; and provide information to the web-based medical application, based on the received medical data, through an application programming interface (API), or with a Transmission Control Protocol/Internet Protocol (TCP/IP) communication.

8. The system of claim 1, wherein at least a portion of the medical application includes a client-server-based medical application; and wherein the instructions to implement the client application, when executed by the at least one processor, cause the at least one processor to perform further electronic operations that:

control access of the client-server-based medical application to the resource of the client operating system; and provide information to the client-server-based medical application, based on the received medical data, through an application programming interface (API), or with a Transmission Control Protocol/Internet Protocol (TCP/IP) communication.

9. The system of claim 2, wherein the instructions to implement the client application, when executed by the at least one processor, cause the at least one processor to perform further electronic operations that:

receive information from the medical application; and provide medical data to the medical application according to a second medical standard based on the received information.

10. The system of claim 9, wherein the first and second medical standards separately include one of a Digital imaging and Communications in Medicine (DICOM) standard, a Health Level Seven (HL7) standard, or an Integrating the Healthcare Enterprise (IHE) standard.

11. The system of claim 10, wherein the first medical standard includes the second medical standard.

12. The system of claim 1, wherein the resource of the client operating system includes a network interface; and wherein the instructions to implement the client application, when executed by the at least one processor, cause the at least one processor to perform further electronic operations that:

restrict access of the medical application to the network interface.

13. The system of claim 1, wherein the medical application includes a plurality of medical applications selectable from a server; and wherein the instructions to implement the client application, when executed by the at least one processor, cause the at least one processor to perform further electronic operations that:

receive an indication of a selection of a first medical application; and provide information to the first medical application based on the received medical data.

14. The system of claim 1, wherein the computing system is connected to a server configured to store a plurality of medical applications including the medical application; and wherein the instructions to implement the client application, when executed by the at least one processor, cause the at least one processor to perform further electronic operations that:

receive an indication of a selection of the medical application;

receive at least a portion of the medical application from the server;

execute at least a portion of the medical application;

receive information from the medical application; and provide medical data to the medical application according to a second medical standard based on the received information.

15. The system of claim 1, wherein the instructions to implement the client application, when executed by the at least one processor, cause the at least one processor to perform further electronic operations that:

receive medical data from a database according to a first medical standard, the medical data including at least one of medical imaging data, patient medical records, or healthcare information;

receive information from the medical application; and provide medical data to the database according to a second medical standard based on the received information.

16. A non-transitory machine-readable storage medium containing instructions to implement a client application that, when executed by at least one processor, causes the at least one processor to perform electronic operations that:

control access of a medical application to a resource of a client operating system;

receive medical data from a data source that is external to the client application and the medical application;

provide information to the medical application based on the received medical data; and control execution of the medical application and control access to the received medical data, to comply with at least one patient data privacy requirement defined by medical informatics standards or medical informatics regulations;

wherein the client cation is provided to computing system as a container that is deployable in the client operating system;

wherein the container provides a virtualized operating system for operation of the medical application and the client application, wherein the virtualized operating system executes within the client operating system, and wherein the virtualized operating system is separated from the client operating system; and wherein the client application and the medical application operate in the virtualized operating system, and wherein the client application and the medical application operate without installation of the client application and the medical application onto the client operating system.

17. The non-transitory machine-readable storage medium of claim 16, wherein the electronic operations that receive the medical data include electronic operations to:

receive medical data according to information communication characteristics defined by a first medical standard.

18. The non-transitory machine-readable storage medium of claim 16, wherein the instructions to implement the client application, when executed by the at least one processor, cause the at least one processor to perform further electronic operations that:

control access to the medical application.

19. The non-transitory machine-readable storage medium of claim 16, wherein the instructions to implement the client application, when executed by the at least one processor, cause the at least one processor to perform further electronic operations that:

receive an indication of a request for metered use of the medical application;

request permission for metered use of the medical application, wherein the metered use includes at least one of a single use, a defined number of uses, unlimited use, or timed use;

receive at least a portion of the medical application in response to the request for metered permission; and execute at least a portion of the medical application.

20. The non-transitory machine-readable storage medium of claim 16, wherein at least a portion of the medical application includes a virtualized medical application; and wherein the instructions to implement the client application, when executed by the at least one processor, cause the at least one processor to perform further electronic operations that:

control access of the virtualized medical application to the resource of the client operating system; and provide information to the virtualized medical application based on the received medical data.

21. A method of operation for a controlled used medical application, the method comprising electronic operations including:

receiving a client application as a container for deployment within a client operating system; and operating the client application in the container, to perform operations including:

controlling access of a medical application to a resource of the client operating system;

receiving medical data from a data source that is external to the client application and the medical application;

providing information to the medical application based on the received medical data; and controlling execution of the medical application and control access to the received medical data, to comply with at least one patient data privacy requirement defined by medical informatics standards or medical informatics regulations;

wherein the container provides a virtualized operating system for operation of the medical application and the client application, wherein the virtualized operating system executes within the client operating system, and wherein the virtualized operating system is separated from the client operating system; and wherein the client application and the medical application operate in the virtualized operating system, and wherein the client application and the medical application operate without installation of the client application and the medical application onto the client operating system.

22. The method of claim 21, the electronic operations further including:

receiving an indication of a request for metered use of the medical application;

requesting permission for metered use of the medical application, wherein the metered use includes at least one of a single use, a defined number of uses, unlimited use, or timed use;

receiving at least a portion of the medical application in response to the request for metered permission; and executing at least a portion of the medical application.

* * * * *

UNITED STATES PATENT AND TRADEMARK OFFICE
CERTIFICATE OF CORRECTION

PATENT NO.           : 9,659,186 B2                                        Page 1 of 1
APPLICATION NO.      : 14/513252
DATED                : May 23, 2017
INVENTOR(S)          : Pinsky et al.

It is certified that error appears in the above-identified patent and that said Letters Patent is hereby corrected as shown below:

In the Claims

In Column 27, Line 1-2, in Claim 6, after "application", delete "using"

In Column 27, Line 43-44, in Claim 10, delete "imaging" and insert --Imaging-- therefor In Column 28, Line 45, in Claim 16, delete "cation" and insert --application-- therefor Signed and Sealed this
Twenty-third Day of January, 2018

Joseph Matal
*Performing the Functions and Duties of the*
*Under Secretary of Commerce for Intellectual Property and*
*Director of the United States Patent and Trademark Office*